United States Patent
Ortiz et al.

(10) Patent No.: US 7,309,341 B2
(45) Date of Patent: Dec. 18, 2007

(54) SINGLE LUMEN ANASTOMOSIS APPLIER FOR SELF-DEPLOYING FASTENER

(75) Inventors: Mark S. Ortiz, Milford, OH (US); Robert Hugh McKenna, Cincinnati, OH (US); William J. Kraimer, Mason, OH (US); Michael J. Stokes, Cincinnati, OH (US); Foster B. Stulen, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 311 days.

(21) Appl. No.: 10/675,497

(22) Filed: Sep. 30, 2003

(65) Prior Publication Data

US 2005/0070921 A1    Mar. 31, 2005

(51) Int. Cl.
*A61B 17/08* (2006.01)
*A61B 17/10* (2006.01)
*A61B 1/32* (2006.01)
*A61M 29/00* (2006.01)
*A61F 2/06* (2006.01)

(52) U.S. Cl. .............. 606/153; 606/151; 606/157; 606/198; 606/139; 600/207; 623/1.11; 623/1.23; 227/176.1

(58) Field of Classification Search ........... 606/153, 606/139, 151, 157, 198; 604/109–113; 600/201, 600/207; 227/176.1, 155, 19; 623/1.11, 623/1.23

See application file for complete search history.

(56) References Cited

U.S. PATENT DOCUMENTS

| | | | |
|---|---|---|---|
| 5,098,388 A * | 3/1992 | Kulkashi et al. ............ 604/158 |
| 5,676,670 A | 10/1997 | Kim | |
| 5,797,920 A * | 8/1998 | Kim ........................ 606/108 |
| 5,855,312 A * | 1/1999 | Toledano ................. 227/176.1 |
| 6,007,544 A | 12/1999 | Kim | |
| 6,171,321 B1 * | 1/2001 | Gifford et al. ............ 606/153 |
| 6,312,446 B1 | 11/2001 | Huebsch et al. | |
| 6,451,029 B1 * | 9/2002 | Yeatman .................. 606/139 |
| 6,485,496 B1 * | 11/2002 | Suyker et al. ............ 606/153 |
| 6,543,456 B1 | 4/2003 | Freeman | |
| 2003/0032967 A1 * | 2/2003 | Park et al. ................ 606/153 |
| 2003/0109893 A1 | 6/2003 | Vargas et al. | |
| 2005/0070926 A1 | 3/2005 | Ortiz | |
| 2005/0070934 A1 | 3/2005 | Tanaka et al. | |
| 2005/0070935 A1 | 3/2005 | Ortiz | |
| 2005/0070939 A1 | 3/2005 | Beaupre | |

OTHER PUBLICATIONS

EPO Search Report, Application No. EP 04 25 6052, Jan. 28, 2005, pp. 1-3.

* cited by examiner

*Primary Examiner*—(Jackie) Tan-Uyen Ho
*Assistant Examiner*—Melissa Ryckman
(74) *Attorney, Agent, or Firm*—Frost Brown Todd, LLC

(57) ABSTRACT

A surgical tool or applier facilitates laparoscopic or endoscopic implantation through a single bodily tissue lumen of an anastomotic ring device for forming a hollow rivet type of attachment between tissue lumens. In addition to forming a puncture between apposite tissue walls at the anastomosis site, the applier assists or wholly actuates the anastomotic ring device and is retracted to deploy the actuated ring device. Illumination incorporated into a distal portion of a cannula enables confirmation of deployment.

5 Claims, 14 Drawing Sheets

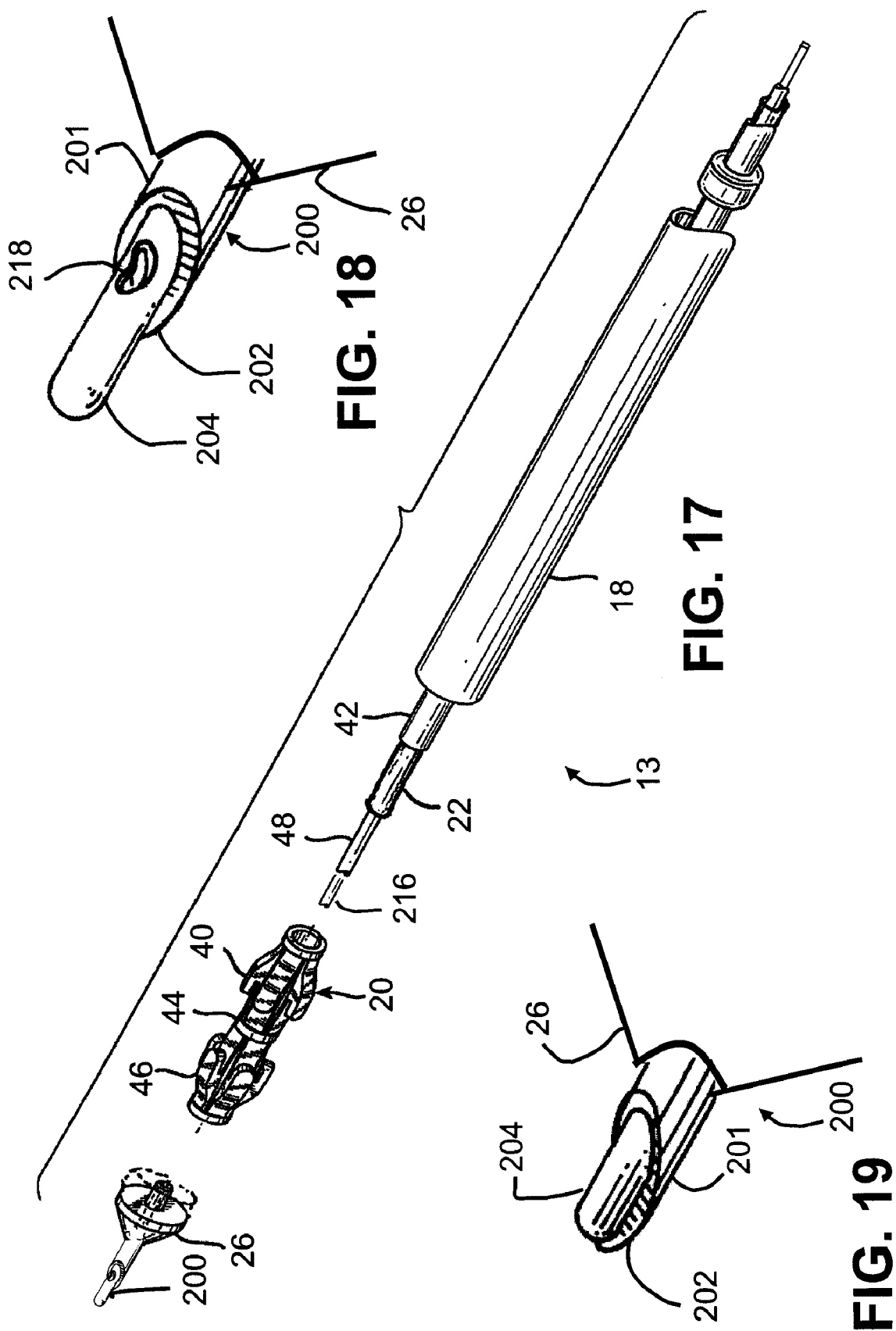

SINGLE LUMEN ANASTOMOSIS APPLIER FOR SELF-DEPLOYING FASTENER

CROSS REFERENCE TO RELATED APPLICATIONS

The present application is related to four co-pending and commonly-owned application filed on even date herewith, the disclosure of each is hereby incorporated by reference in its entirety:

"Anastomosis Wire Ring Device", Ser. No. 10/674,371 to Don Tanaka, Mark Ortiz and Darrel Powell;

"Applier For Fastener For Single Lumen Access Anastomosis", Ser. No. 10/675,077 to Mark Ortiz;

"Unfolding Anastomosis Ring Device", Ser. No. 10/675,091 to Jean Beaupre; and

"Single Lumen Access Deployable Ring for Intralumenal Anastomosis", Ser. No. 10/675,075 to Mark Ortiz.

FIELD OF THE INVENTION

The present invention relates, in general, to surgery and, more particularly, to a method of performing a surgical procedure on the digestive system.

BACKGROUND OF THE INVENTION

The percentage of the world population suffering from morbid obesity is steadily increasing. Severely obese persons are susceptible to increased risk of heart disease, stroke, diabetes, pulmonary disease, and accidents. Because of the effect of morbid obesity to the life of the patient, methods of treating morbid obesity are being researched.

Numerous non-operative therapies for morbid obesity have been tried with virtually no permanent success. Dietary counseling, behavior modification, wiring a patient's jaws shut, and pharmacologic methods have all been tried, and though temporarily effective, failed to correct the condition. Further, introducing an object in the stomach, such as an esophago-gastric balloon, to fill the stomach have also been used to treat the condition; however, such approaches tend to cause irritation to the stomach and are not effective long-term.

Surgical treatments of morbid obesity have been increasingly used with greater success. These approaches may be generalized as those that reduce the effective size of the stomach, limiting the amount of food intake, and those that create malabsorption of the food that it is eaten. For instance, some patients benefit from adjustable gastric bands (AGB) that are advantageously laparoscopically placed about the stomach to form a stoma of a desired size that allows food to fill an upper portion of the stomach, causing a feeling of satiety. To allow adjustment of the size of the stoma after implantation, a fluid conduit communicates between an inwardly presented fluid bladder of the AGB to a fluid injection port subcutaneously placed in front of the patient's sternum. A syringe needle may then inject or withdraw fluid as desired to adjust the AGB.

Although an effective approach to obesity for some, other patients may find the lifestyle changes undesirable, necessitated by the restricted amount of food intake. In addition, the medical condition of the patient may suggest the need for a more permanent solution. To that end, surgical approaches have been used to alter the portions of the stomach and/or small intestine available for digesting food. Current methods of performing a laparoscopic anastomoses for a gastric bypass include stapling, suturing, and placing biofragmentable rings, each having significant challenges. For instance, suturing is time consuming, as well as being technique and dexterity dependent. Stapling requires placement of an anvil, which is a large device that cannot be introduced through a trocar port. Having to introduce the port through a laparotomy presents an increased incidence of wound site infection associated with intralumenal content being dragged to the laparotomy entry site.

As an example of the latter approach, in U.S. Pat. No. 6,543,456 a method for gastric bypass surgery includes the insertion of proximal and distal anastomosis members (e.g., anvils) transorally with grasping forceps. The stomach and the small intestine are transected endoscopically by a surgical severing and stapling instrument to create a gastric pouch, a drainage loop, and a Roux limb. An endoscopically inserted circular stapler attaches to the distal anastomosis member to join the drainage loop to a distal portion of the intestine, and the circular stapler attaches to the proximal anastomosis member to join the Roux limb to the gastric pouch. Thereafter, the anastomosis members are removed to create an orifice between joined portions of the stomach and intestine. This method reduces the number of laparoscopic ports, avoids a laparoscopic insertion of an anastomosis instrument (e.g., circular stapler) into an enlarged surgical port, and eliminates the need for an enterotomy and an enterotomy closure.

While methods such as that described are a marked improvement over generally known gastric bypass and similar surgical treatments for morbid obesity, it would be desirable to achieve a gastric bypass with yet fewer procedural steps and with fewer laparoscopic insertions. Such an approach is described in U.S. patent application Publ. No. US 2003/0032967 to Park et al., wherein gastrointestinal or enteric (including biliary) anastomosis is achieved by insertion of a sheath that perforates the walls of two tissue passages, such as the stomach and small intestine. A three-dimensional woven tube of wire of having a thermal shape memory effect (SME) is presented by a cannula of the sheath on both sides of the openings. Use of SME material in a cuff-like arterial bypass has been previously used, as described in U.S. Pat. Nos. 5,676,670, 5,797,920 and 6,007,544. Deployment of the woven tube causes the outer loops or ends of the tube to fold or loop back to hold the luminal interface of the anastomosis site in apposition. Thereby, the need for a mechanical compression component in a delivery system is reduced or avoided, reducing the size and complexity of the delivery device.

While this generally known ring device is a significant advancement in the treatment of morbid obesity, it is believed that further improvements would be desirable for clinical effectiveness. In particular, the known ring device is a woven tube, or stent, that is purported to be a self-actuating anastomotic ring. Thus, an applier described for inserting the known ring device merely positions the ring device at the anastomotic site and deploys the ring device by pushing it off of a cannula, relying upon SME attributes of the ring device to cause actuation. Unfortunately, the generally known ring device sometimes will not actuate or transform from its stressed cylindrical state to its relaxed clamping state, perhaps due to irregularities in undulations of its woven designs create friction. One particular difficulty of known SME anastomotic rings are that they are designed to move from a generally cylindrical shape to a hollow rivet shape ("ring shape") by having wires that form the device move across one another. In particular, wires must move within a nodal point (i.e., an indentation or valley) created by the wire bend and must climb back out of the indentation.

In some instances, the device fails to fully actuate on its own due to these sources of friction.

While improvements to the ring device are also desirable, what would mitigate the shortcomings of the generally known ring device is a surgical tool, or applier, that affirmatively and rapidly forms the attachment at an anastomotic surgical site, without having to wait for SME actuating to slowly, if at all, effect attachment. However, such an applier would advantageously allow a single lumen access, unlike the previously known anastomosis procedures that required insertion of anvils and circular staplers.

Moreover, it is believed that having to rely upon an SME actuation sufficiently strong to move from the stressed, unactuated position to the relaxes, actuated position limits the range of material properties and dimensions that otherwise may be selected. For instance, a thinner gauge wire strand may advantageously provide sufficient holding strength until the anastomosis attachment heals, yet releases easily later for letting the now unnecessary ring device to pass out of the patient. Yet, this thinner gauge wire strand would be unable to incorporate sufficient SME strength to overcome internal friction and to draw together apposite tissue walls during actuation.

In addition, a current challenge for using a single lumen anastomosis procedure is that it is desired for clinical efficiency and for minimizing patient recovery time that the anastomosis site be approached from one side of the apposite pair of tissue walls of two adjacent tissue passages (e.g., stomach and small intestine). Yet, only one of the tissue walls and a proximal side of a deployed ring device are readily visible from this vantage point, when viewed by an endoscope or similar optical imaging device. Confirming that a successful anastomotic attachment has occurred is highly desirable.

Consequently, there is a general need for an approach to anastomosis that will use existing trocar ports (e.g., 12 mm size) with a minimum of suturing. Moreover, aspects of the method should have application to endoscopic surgery. To that end, a significant need exists for an anastomosis device that reliably and effectively deploys and actuates to eliminate the need for surgical stapling and suturing to form an anastomosis.

BRIEF SUMMARY OF THE INVENTION

The invention overcomes the above-noted and other deficiencies of the prior art by providing a surgical tool or applier that facilitates laparoscopic or endoscopic implantation through a single bodily tissue lumen of an anastomotic ring device for forming a hollow rivet type of attachment between tissue lumens. In addition to forming a puncture between apposite tissue walls at the anastomosis site, the applier assists or wholly actuates the anastomotic ring device and is retracted to deploy the actuated ring device.

In one aspect of the invention, a surgical instrument has an actuating member that is moveable between a cylindrical, unactuated position and a hollow rivet forming shape for implanting an anastomotic ring device. A handle of the instrument has an actuation mechanism produces a compressive actuating force that is transferred down an elongate cannula that distally supports the actuating member to actuate the actuating member. Thereby, the anastomotic ring device is affirmatively placed into position without having to rely solely upon a self-actuating capability of the ring device.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 17 is perspective, exploded and partially cutaway view of a distal portion of the applier of FIG. 15.

FIG. 18 is a perspective view of the vertress needle distal piercing tip in an unactuated position for shielding a cutting surface and presenting a gas exit hole for lumen insufflation.

FIG. 19 is a perspective view of the vertress needle distal piercing tip in an actuated position for exposing the cutting surface for forming an anastomosis site between tissue lumens.

DETAILED DESCRIPTION OF THE INVENTION

Figure 1:
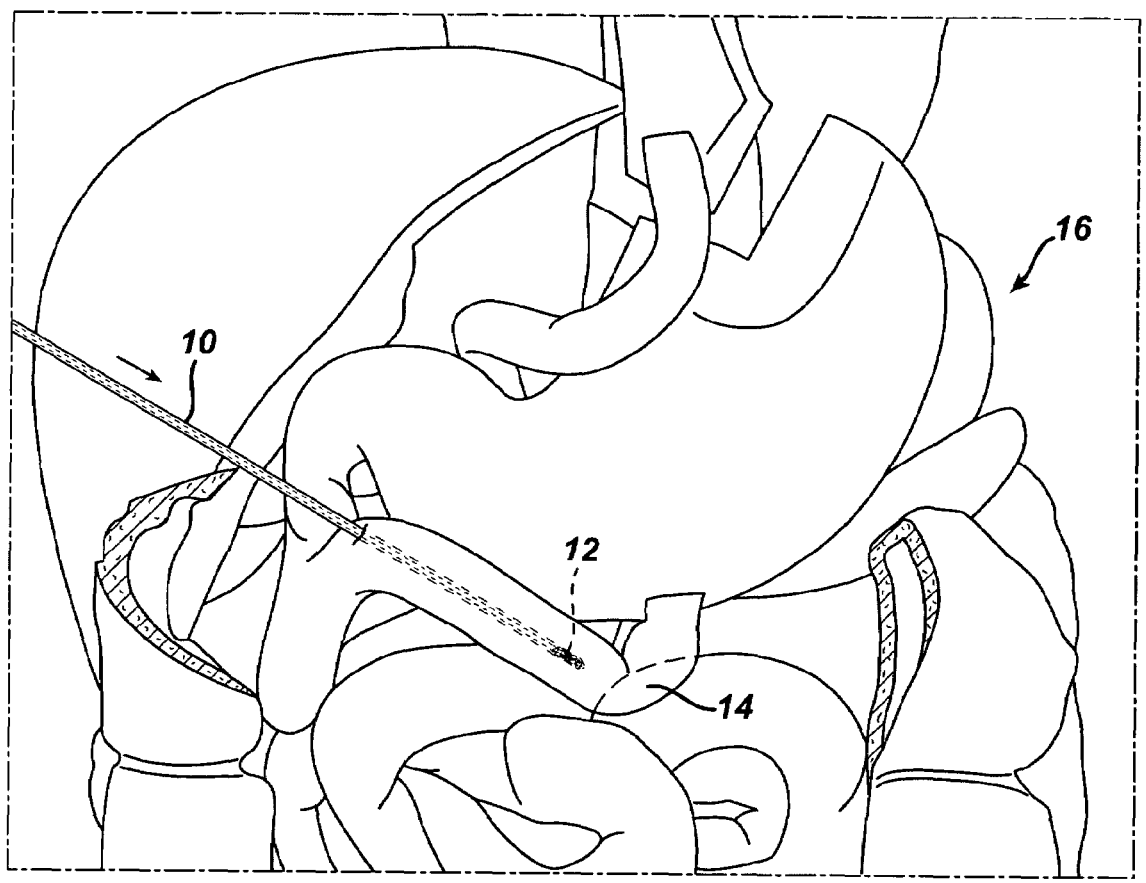
FIG. 1 is perspective view of an applier having an anastomotic ring device installed thereon being inserted laparoscopically to an anastomosis target site on each of two portions of a patient's small intestine.

Turning to the Drawings, wherein like numerals denote like components throughout the several views, FIG. 1 depicts an applier 10 that advantageously laparoscopically or endoscopically deploys and actuates an anastomotic ring device 12 from a generally cylindrical shape to one having properties of a hollow rivet, or ring, capable of forming an astomotic attachment at an anastomosis target site, such as in a bariatric gastric bypass of a morbidly obese patient 16. In the illustrative version, the anastomotic ring device 12 comprises a shape memory effect (SME) material such as nitinol that further assists in actuation to an engaging hollow rivet shape.

It will be appreciated that the terms "proximal" and "distal" are used herein with reference to a clinician gripping a handle of the applier 10. It will be further appreciated that for convenience and clarity, spatial terms such as "right", "left", "vertical" and "horizontal" are used herein with respect to the drawings. However, surgical instruments are used in many orientations and positions, and these terms are not intended to be limiting and absolute. In addition, aspects of the invention have application to surgical procedures performed endoscopically and laparoscopically, as well as an open procedure. Use herein of one of these or similar terms should not be construed to limit the present invention for use in only one category of surgical procedure.

Anastomotic Ring Device Applier.

Figure 2:
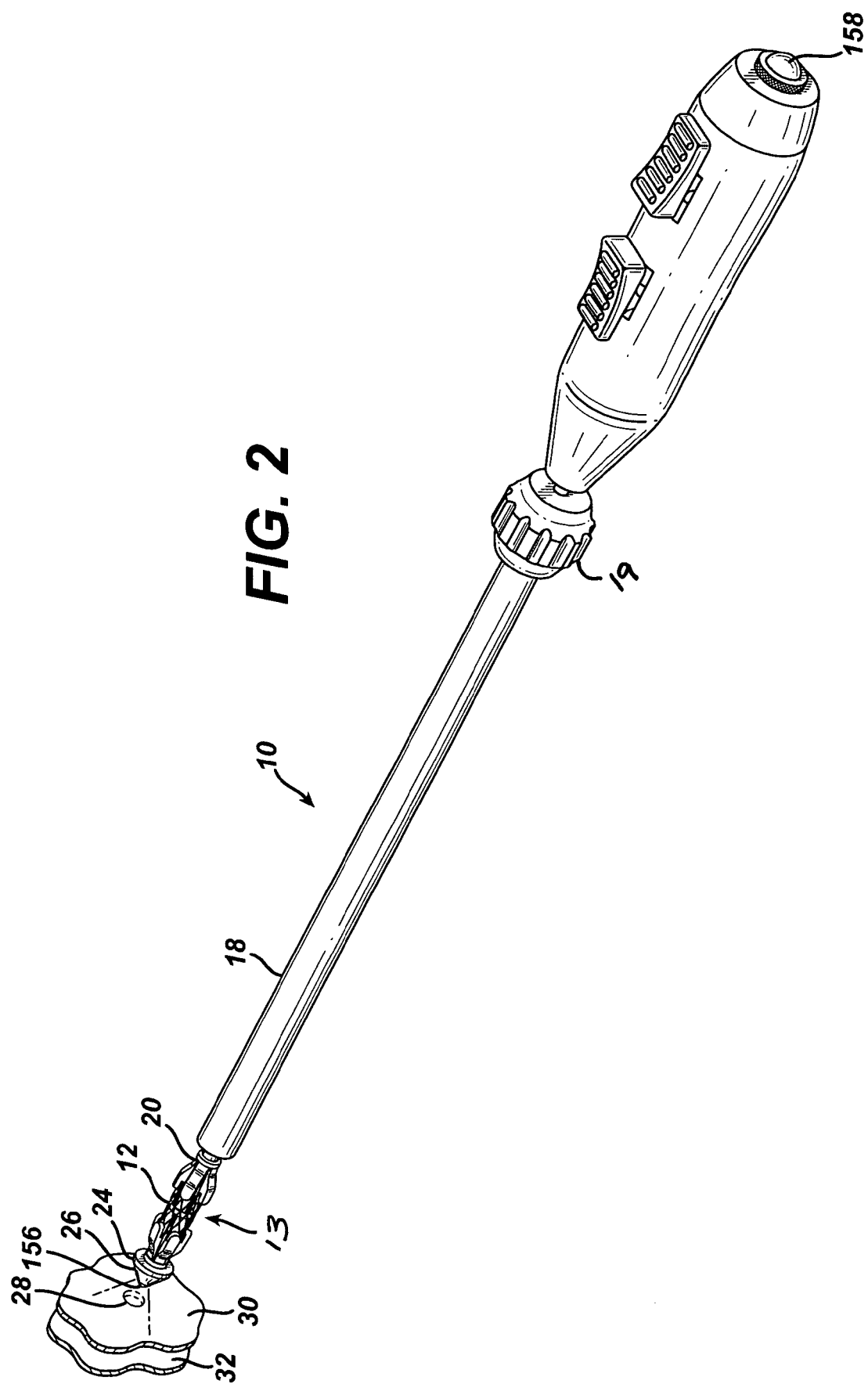
FIG. 2 is a perspective detail view of the applier with sheath retracted and anastomosis target site of FIG. 1, depicting the anastomotic ring device in its undeployed, unactuated state.

In FIG. 2, the applier 10 has the anastomotic ring device 12 advantageously retained in a generally cylindrical shape upon a cannula 13 protected by an outer tube (or sheath) 18 that covers the ring device 12 until a knob 19 is rotated, drawing back the outer tube 18 to expose the ring device 12 prior to actuation. The ring device 12 is received upon a molded actuation member 20 that is connected at its midpoint to a stationary tube 22. Distal to the molded actuation member 20 is a tapered tip 24. This tapered tip 24 may include a distal piercing surface 26 to assist in forming an anastomotic opening 28 through apposite tissue walls 30, 32 of two gastrointestinal passages. As discussed below, the tapered tip 24 may advantageously include illumination features that allow confirmation of placement and actuation of the anastomotic ring device 12 when viewed from a proximal direction through translucent tissue walls 30, 32.

The molded actuation member 20 may be formed as a generally rectangular piece that is wrapped around a mandrel. Then the longitudinal edges that come together may be adhered or fused together. Alternatively, snap rings may be attached over each longitudinal end (i.e., proximal and distal) and the midpoint to hold the molded actuation member 20 together.

With reference to FIGS. 2-5, a handle 34, proximal to the cannula 13, includes a pair of longitudinally aligned triggers 36, 38. The proximal trigger 36, shown at its most proximal, unfired position, is coupled to proximal leaves 40 of the molded actuation member 20 via an intermediate tube 42 of the cannula 13. Distal movement of the proximal trigger 36 thus causes longitudinal distal movement of the intermediate tube 42 and proximal leaves 40, which outwardly actuate like an umbrella by a cantilevered, hinged relationship to a central portion 44 of the molded actuation member 20, which in turn is mechanically grounded to a distal end of the stationery tube 22 that extends out of the intermediate tube 42. Similarly, the distal trigger 28, shown at its most distal, unfired position, is coupled to distal leaves 46 of the molded actuation member 20 via an internal tube 48 that is coupled for movement within and extends distally out of the stationary tube 22. Proximal movement of the distal trigger 38 causes longitudinal proximal movement of the internal tube 48 and distal leaves 50 of the molded actuation member 20, which outwardly actuate by a hinged relationship to the central portion 44.

It should be appreciated that thus either trigger 36, 38 may be moved individually to actuate only a proximal or a distal portion of the actuating member 20. Thus, the proximal leaves 40 may be actuated within a proximal lumen in order to use the cannula 13 to position the proximal lumen to the distal lumen prior to inserting the tapered tip 24 into the distal lumen. Alternatively, the cannula 13 may be inserted into the distal lumen, the distal leaves 46 may be actuated, and the distal lumen drawn back into contact with the proximal lumen.

Inserting the cannula 13 into the distal lumen and later withdrawing the cannula 13 from both the distal and proximal lumens is facilitated by incorporating a tapered tip 24 with a distal piercing tube 201 of a veress needle 200 that avoids inadvertent damage to tissue and may advantageously inflate the lumens, as depicted in greater detail in FIGS. 15-19. The distal piercing tube 201 of the veress needle 200 has a syringe knife tip 202 within which a ball tip 204 translates. As the veress needle 200 is pressed against the tissue walls 30, 32, the ball tip 204 springedly withdraws into the distal piercing tube 201 of the veress needle 200 exposing the syringe knife tip 202 (FIG. 19). A spring 206 has a distal end received by a cylindrically narrowed portion 208 formed around a proximal portion of a generally cylindrical bobbin 210 that longitudinally reciprocates within a cylindrical bobbin cavity 212 formed in an aft portion of a handle 214. A proximal end of the spring 206 abuts a proximal inner surface of the bobbin cavity 212, urging the bobbin 210 distally. Once through, tissue more distal is generally not positioned under tension and is displaced by the extended ball tip 204 rather than traumatically encountering the knife tip 202 (FIG. 18). The veress needle 200 may advantageously be in pneumatic communication with a hollow internal tube 216 with the ball tip 204 presenting a lateral orifice 218 when extended. Thus, air pressure may be introduced into the proximal and distal lumens so that the actuation member 20 may actuate without being impeded by collapsed tissue and also be withdrawn without impediment. An air port 219 on the handle 214 that communicates with the veress needle 200 provides a port for the insufflation. For a relatively small port (e.g., 1/16 inch), the port may be left unclosed when not in use without allowing a significant amount of air loss through the instrument 10.

Figure 3:
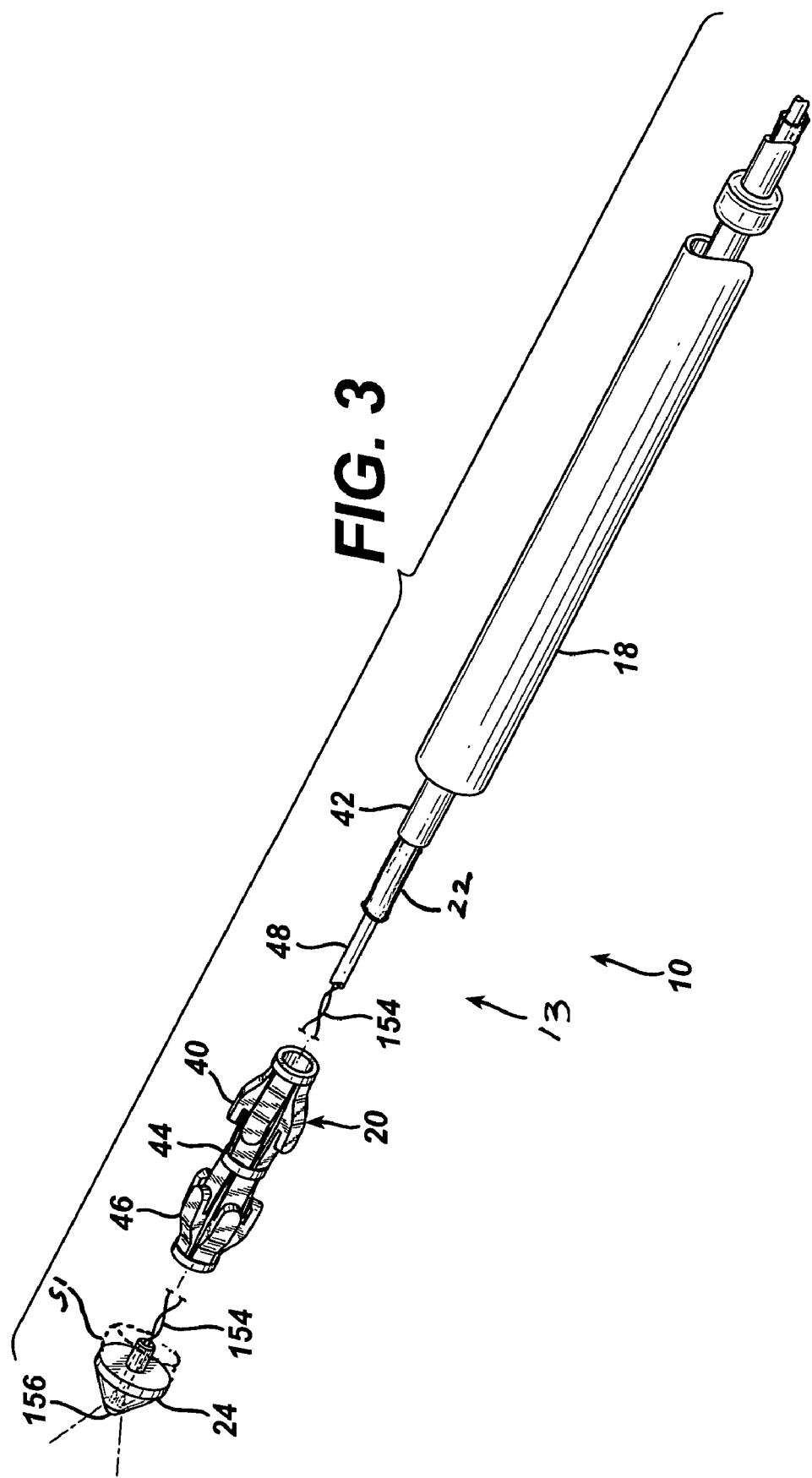
FIG. 3 is a perspective, exploded and partially cutaway view of a distal portion of the applier of FIG. 1.

As depicted in FIG. 3 in phantom, the tapered tip 24 may further include a distal sheath 51 that cooperates with the outer tube 18 to shield the actuating member 20 during insertion and removal from the patient.

Figure 4:
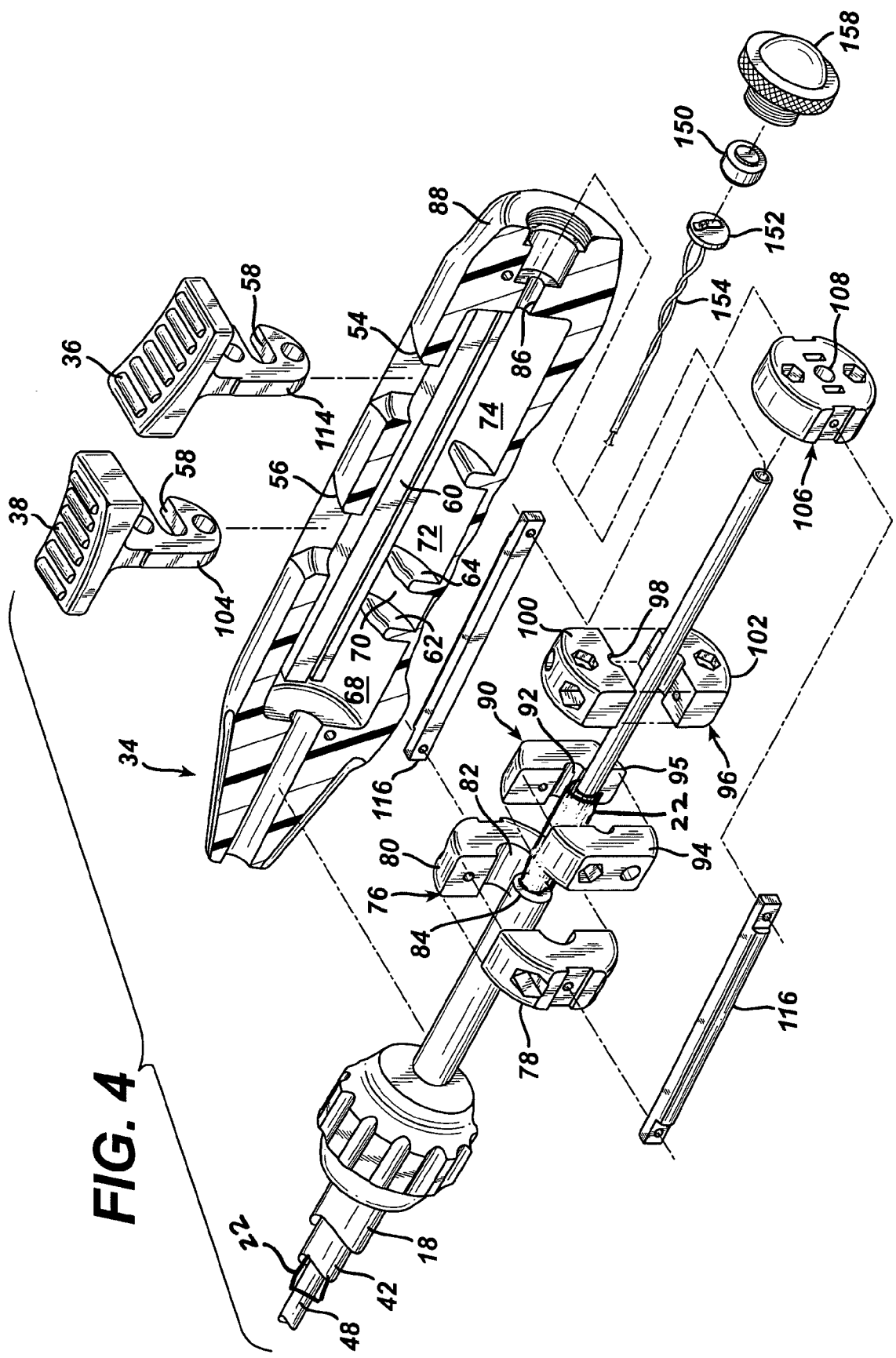
FIG. 4 is a perspective, exploded view of a proximal portion of the applier of FIG. 1 with a left housing half omitted.
Figure 5:
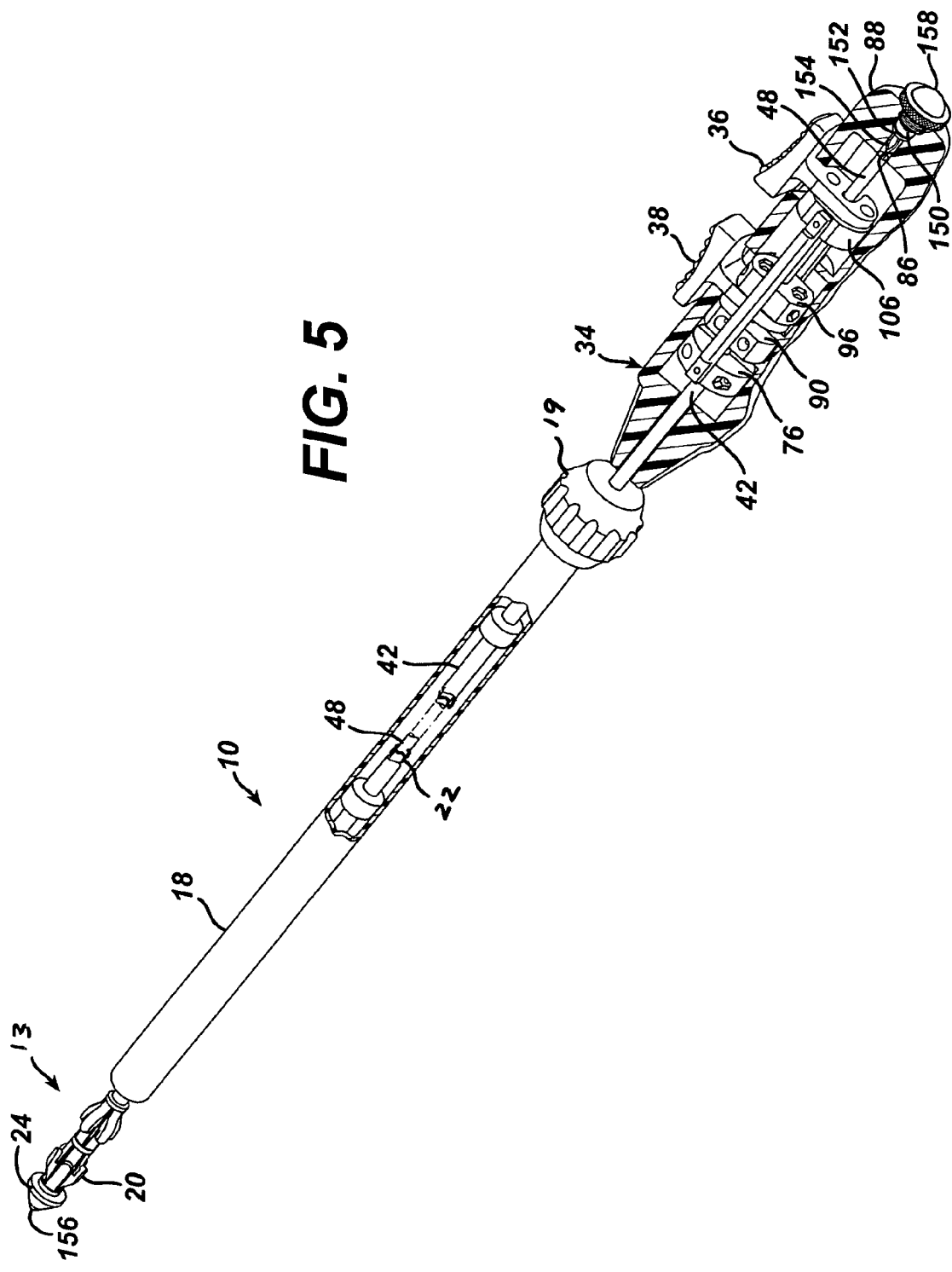
FIG. 5 is perspective view of the applier of FIG. 1 with the left housing half omitted and an outer tube of the cannula partially cutaway to expose an intermediate tube and inner rod that actuate a molded actuating member that actuates the omitted anastomotic ring device, also to expose a deployment illuminator that allows confirming actuation of an anastomotic ring device by viewing through the translucent tissue walls.

As best viewed in FIGS. 4-5, within the handle 34, a cavity 52 includes proximal and distal apertures 54, 56 to allow the longitudinal movement of the proximal and distal triggers 36, 38 respectively. Each trigger 36, 38 includes a right opening aperture 58 that engage for longitudinal movement a leftward projecting track 60 formed within the cavity 52 of a right half shell of the handle 34.

Moving from most distal to most proximal, a first, second and third lateral ridge 62, 64, 66 across the bottom of the cavity 52 define a first, second, third, and fourth cavity segment 68, 70, 72, 74 respectively. A first block 76, formed from left and right halves 78, 80 is positioned for movement within the first cavity segment 68. A longitudinal central hole 82 defined between the two halves 78, 80 engages and moves with a terminating proximal end 84 of the intermediate tube 42.

The stationary tube 22 passes out proximally from the intermediate tube 42 into the second cavity segment 70. A second spacer block 90 locked within the second cavity segment 70 has a longitudinal central hole 92 defined between its left and right halves 94, 95 that engages the stationary tube 22, locking it into place relative the handle 34.

The internal tube 48 passes proximally out of the stationary tube 22 on through the third and fourth cavity segments 72-74 into sliding contact with a hole 86 passing through a proximal end 88 of the handle 34. A third sliding block 96 has a longitudinal central hole 98 defined between its upper and lower halves 100, 102 that engage and move with the internal tube 48. A lower portion 104 of the distal trigger 38 is attached to a distal face of the third sliding block 96. A fourth sliding block 106 within the fourth cavity segment 74 has a longitudinal central hole 108 that slidingly contacts the internal tube 48. A lower portion 114 of the proximal trigger 36 is attached to a proximal face of the fourth sliding block 106. A link 116 is attached to the left sides of the first and fourth sliding blocks 76, 106.

Figure 6:
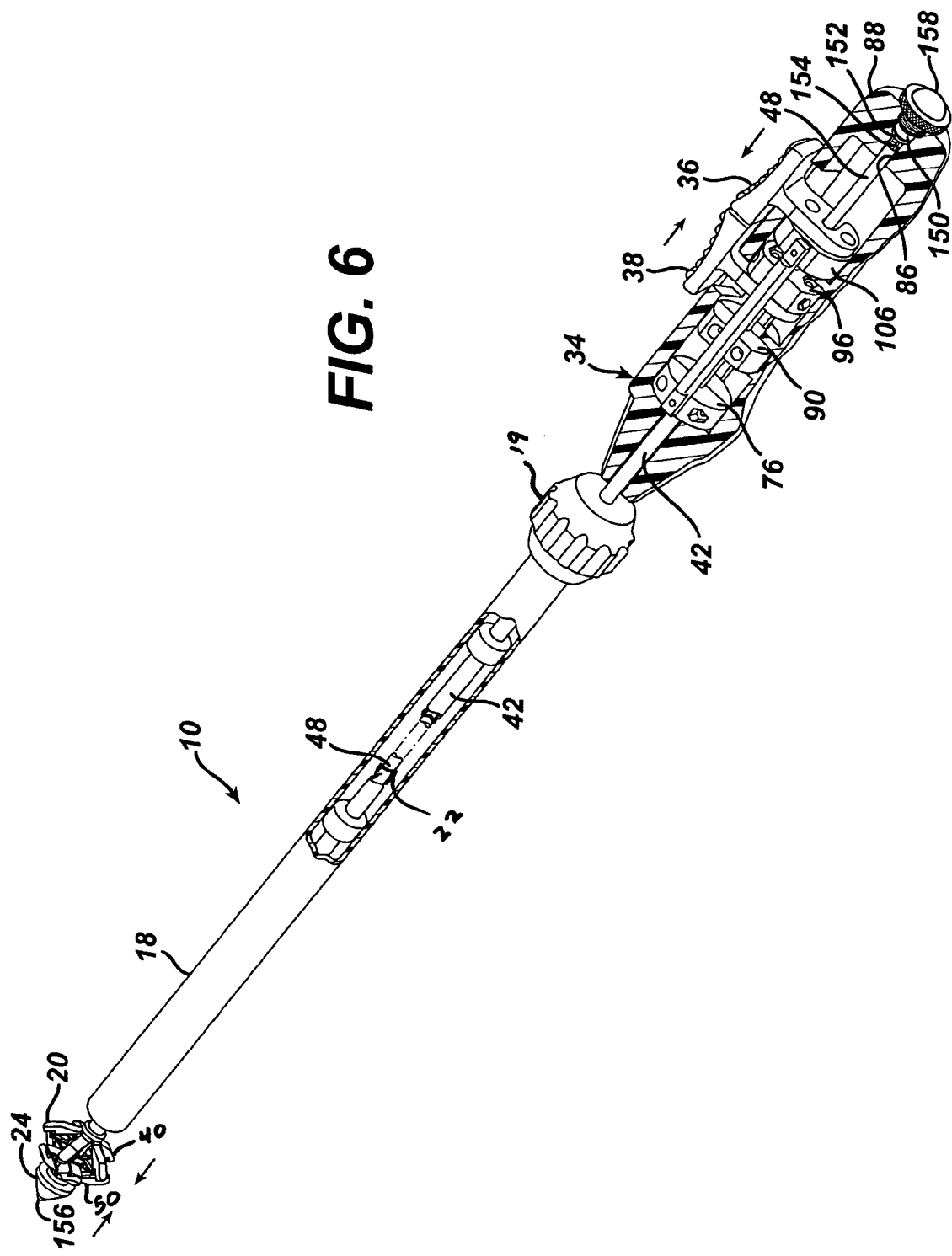
FIG. 6 is a perspective view of the applier of FIG. 5 with the triggers and molded actuating member in an actuated position.

In FIG. 6, the triggers 36, 38 have been slid toward one another to actuate the molded actuating member 20. Specifically, the distal trigger 38 has been moved proximally, moving the third sliding block 96 and internal tube 48, the distal terminating end of the latter being attached to tapered tip 24. The tapered tip thus moves toward the distal end of the intermediate tube 42. The proximal trigger 36 has been moved distally, moving fourth sliding block 106, link 116, first sliding block 76, and intermediate tube 42 also distally. The distal portion of the molded actuating member 20 is compressed between the inwardly moving tapered tip 24 and the central portion 44 that is arrested by the stationary tube 22. The distal leaves 50 actuate lateral to the longitudinal axis, and move toward and interdigitate with the proximal leaves 40, the latter having been actuated by distal movement of the intermediate tube 48 compressing against the central portion 44. This movement expedites actuating of an anastomotic ring device (not shown in FIG. 6).

Figure 8:
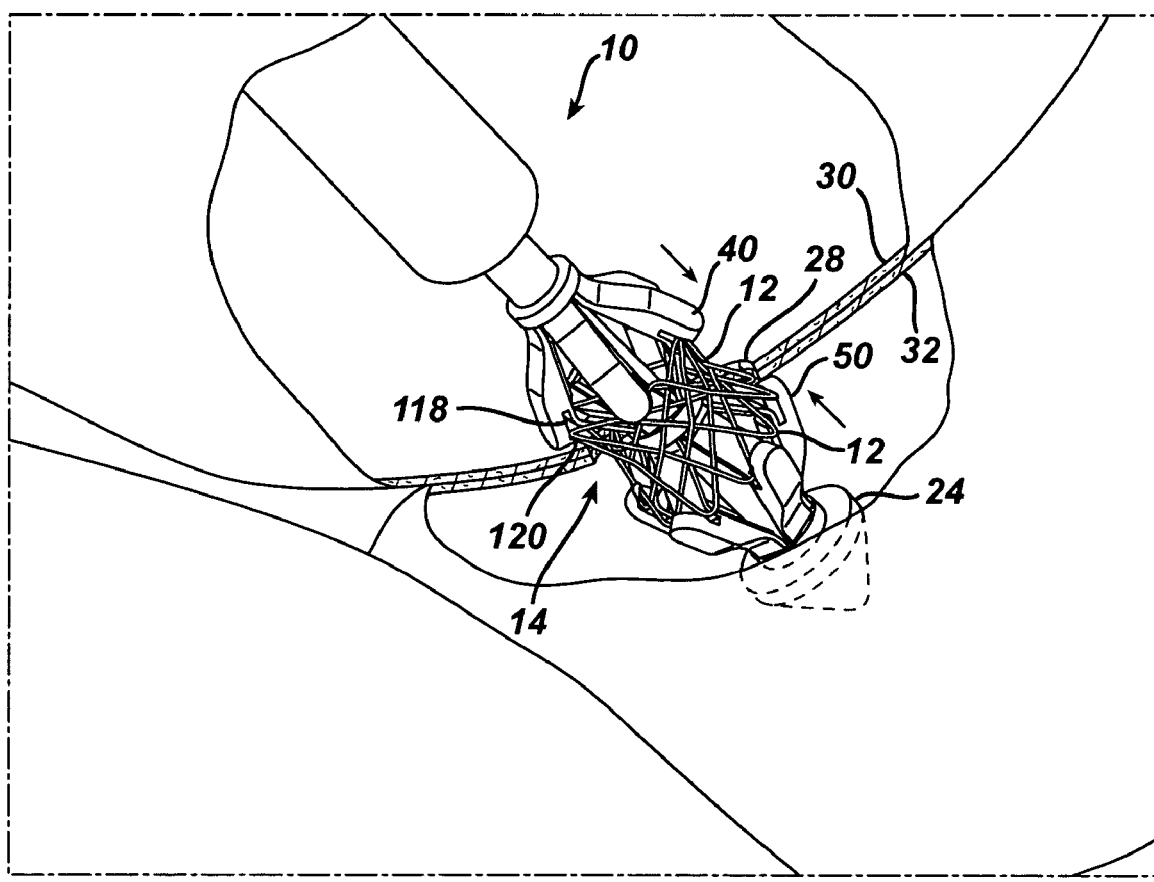
FIG. 8 is a detail perspective view of a distal portion of the applier of FIG. 7 with tissue walls partially cutaway.
Figure 9:
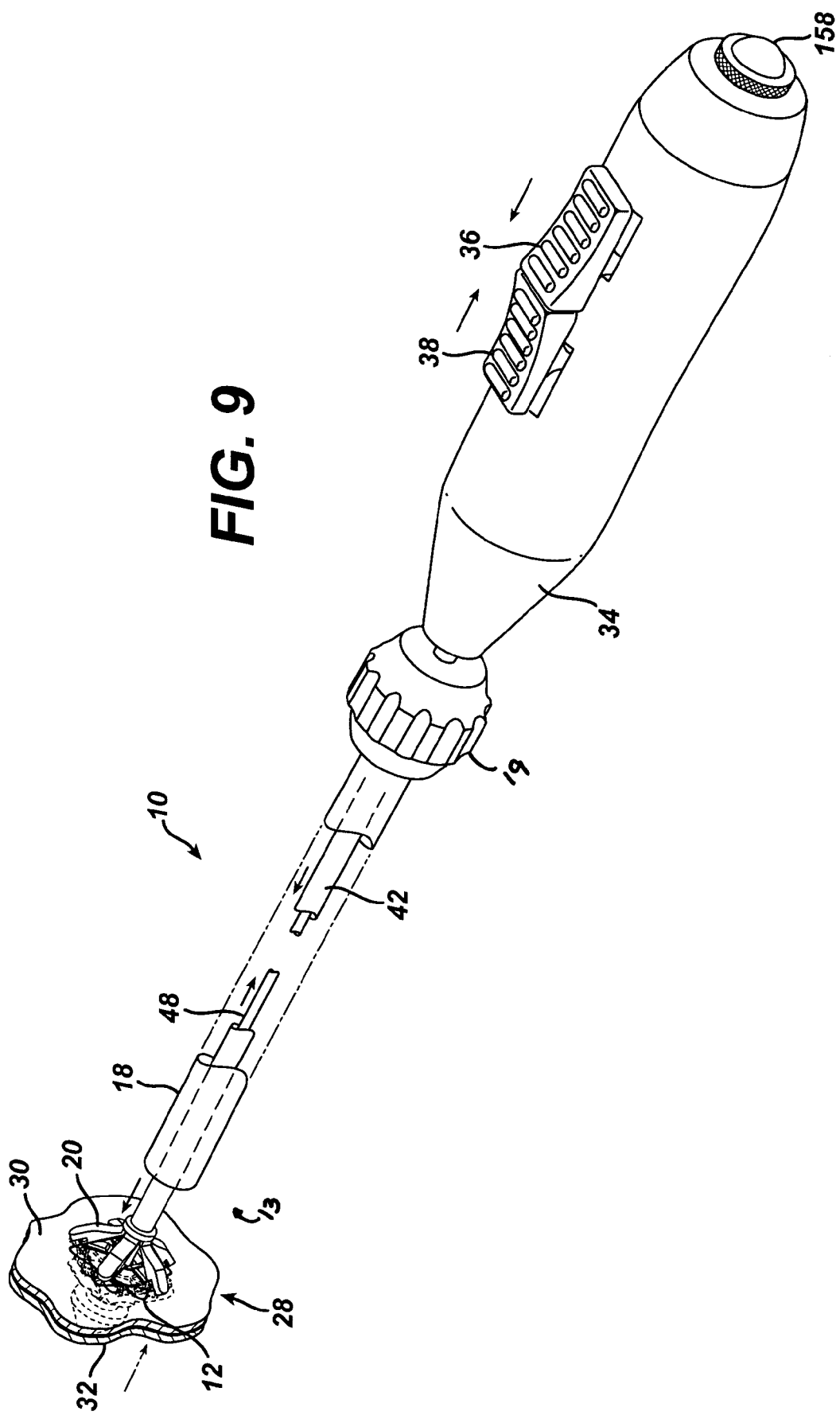
FIG. 9 is a perspective view of the applier of FIG. 1 in a fully actuated state.
Figure 10:
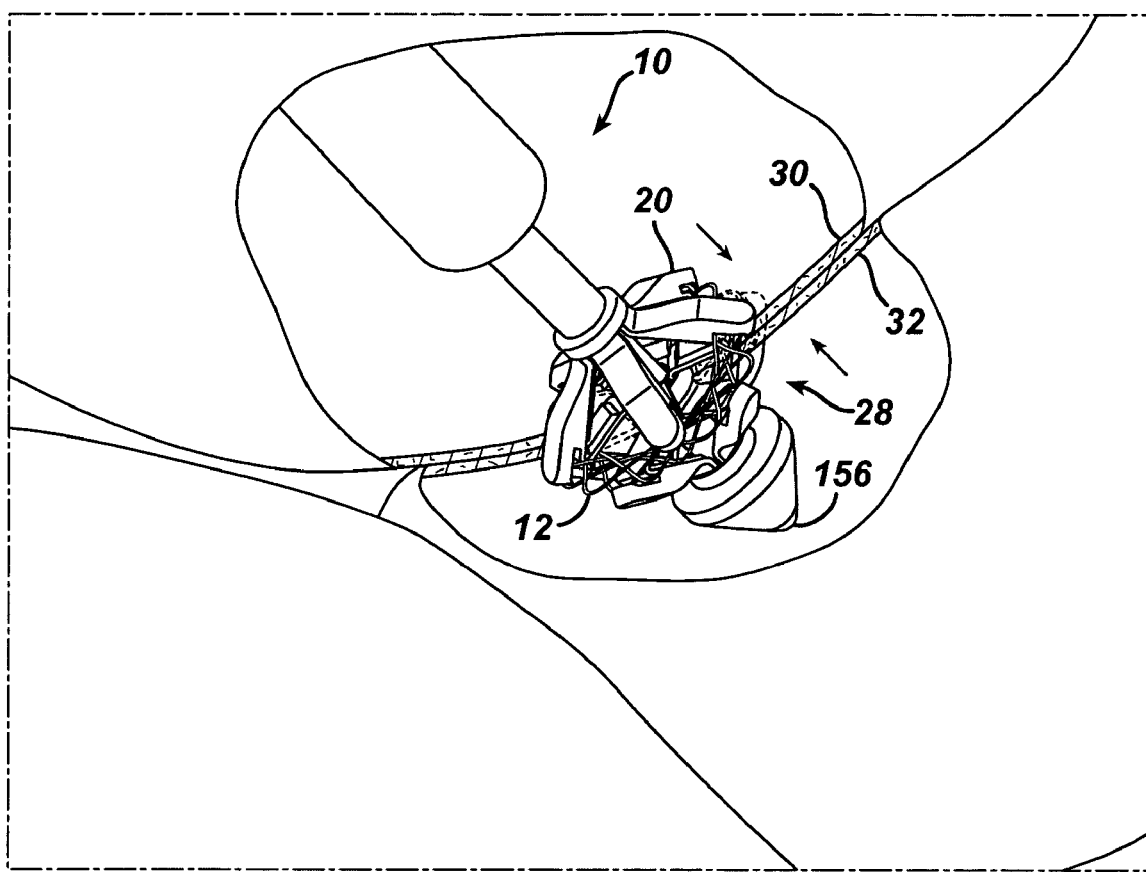
FIG. 10 is a detail perspective view of the distal portion of the applier of FIG. 9 with tissue walls partially cutaway.
Figure 11:
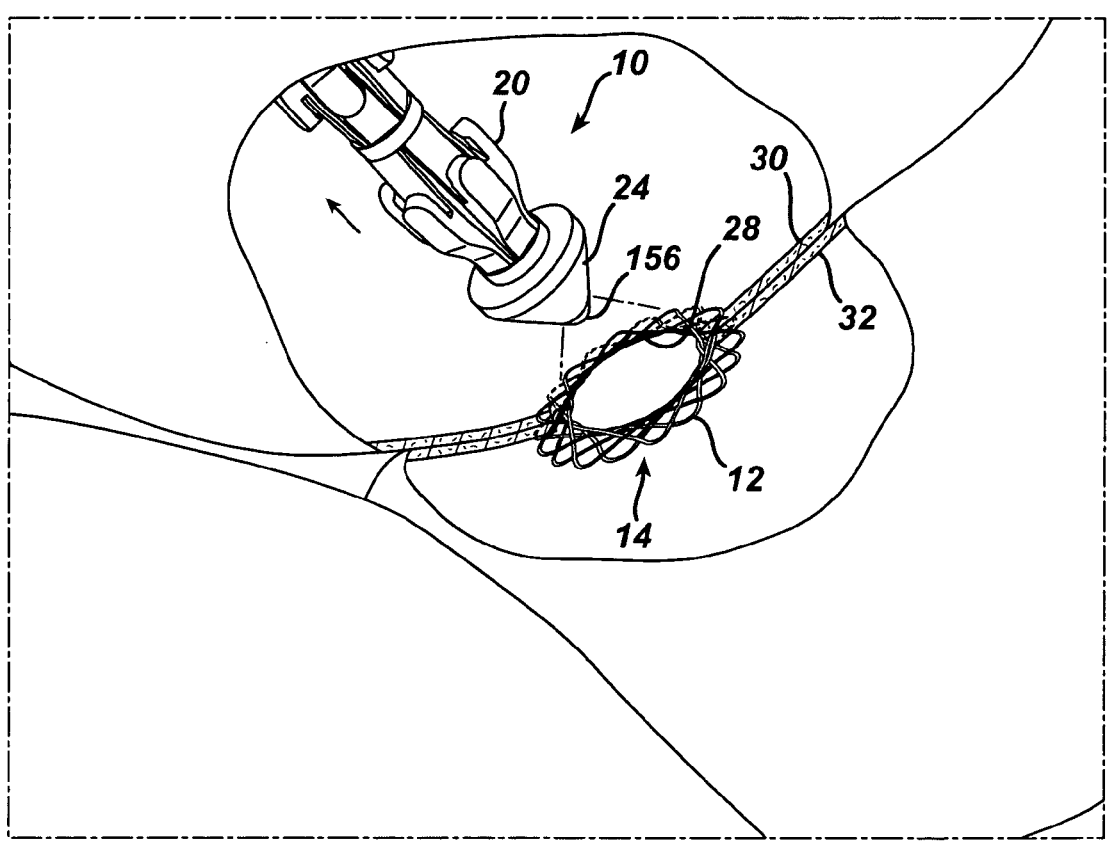
FIG. 11 is a detail perspective view of the distal portion of the applier returned to unactuated state and withdrawn proximally to deploy the actuated anastomotic ring device.
Figure 12:
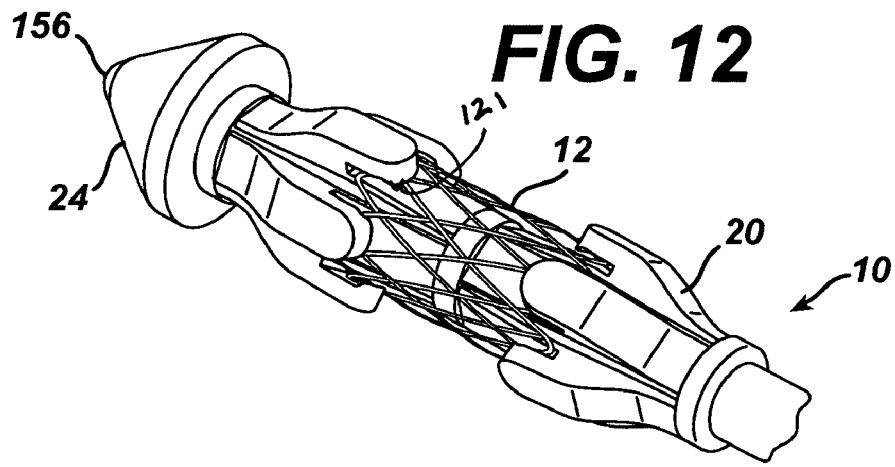
FIGS. 12-14 are detail perspective views of the applier of FIG. 1 in an unactuated, partially actuated, and actuated state shown with retention features.
Figure 13:
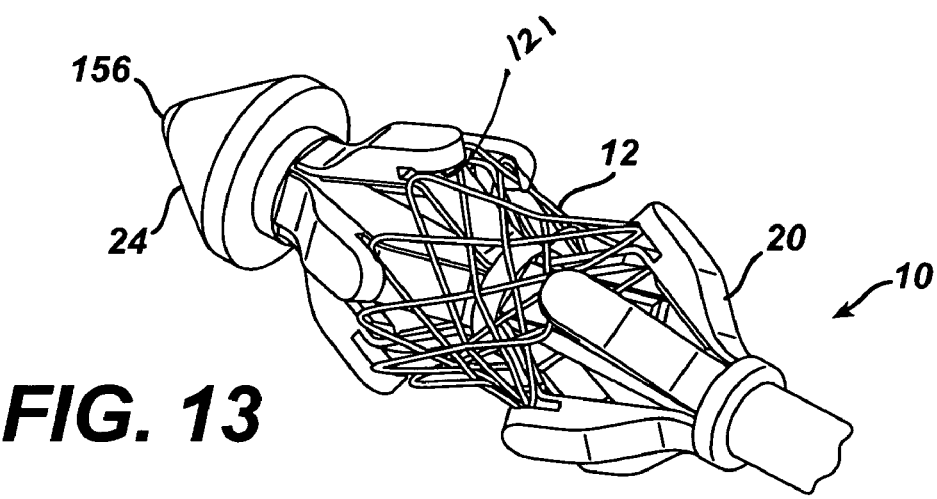
Figure 14:
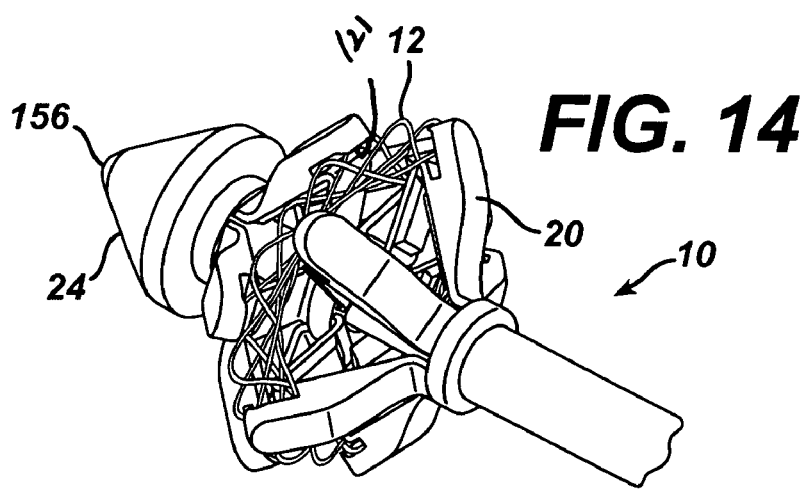
Figures 15, 16:
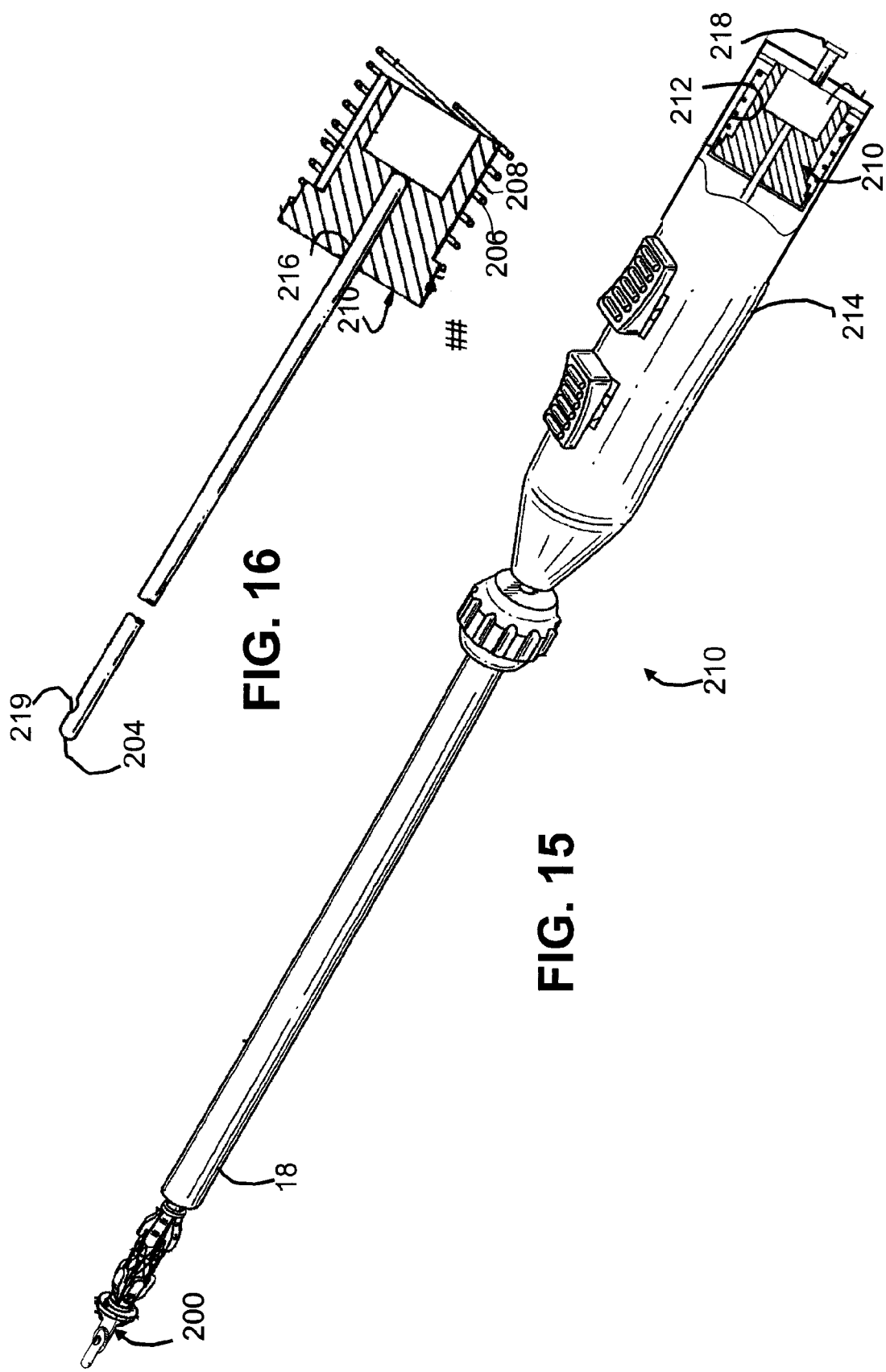
FIG. 15 is an isometric view of an applier incorporating a veress needle distal piercing tip that facilitates insufflation of a pierced tissue lumen and avoids inadvertent tissue damage.
FIG. 16 is a longitudinal cross sectional view of a veress needle bobbin of the applier of FIG. 15.

In use, the tapered tip 24 of the applier 10 is inserted through a trocar port into a tissue passage that has been placed proximate to another tissue passage that are to be anastomotically joined (See FIGS. 1-2). The tapered tip 24 and a distal half of the molded actuating member 20 and anastomotic ring device 12 are inserted through an anastomotic opening 28 formed therebetween and then the applier is actuated, with a partially actuated applier 10 being depicted in FIGS. 7-8. Positioning of the distal and proximal lumens is facilitated by separately actuating half of the actuating member 20 and by inflating the lumens by passing pressurized air through the instrument 10. With particular reference to FIG. 8, the proximal and distal leaves 40, 50 are shown as having gripping slots 118 that grip respective petals 120 of the anastomotic ring device 12, especially in its unactuated, generally cylindrical shape. In FIGS. 12-14, an inwardly directed retention tip 121 or other gripping features in the gripping slots 118 may be incorporated to enhance retention. These gripping slots 118 assist in preventing the anastomotic ring device 12 from slipping off of the applier 10 or being inappropriately placed thereon for actuation. In FIGS. 9-10, the applier 10 has been fully actuated, forming the anastomotic ring device 12 into a hollow rivet shape to form the anastomotic attachment between tissue walls 30, 32. The fully actuated proximal and distal leaves 40, 50 cause the petals 120 to disengage from the gripping slots 118. Thereafter, the applier 10 is returned to an unactuated condition and the actuated anastomotic ring device 12 deployed by withdrawing the tapered tip 24 from the anastomotic opening 28 and ring device 12, as depicted in FIG. 11.

Deployment Illumination.

Figure 7:
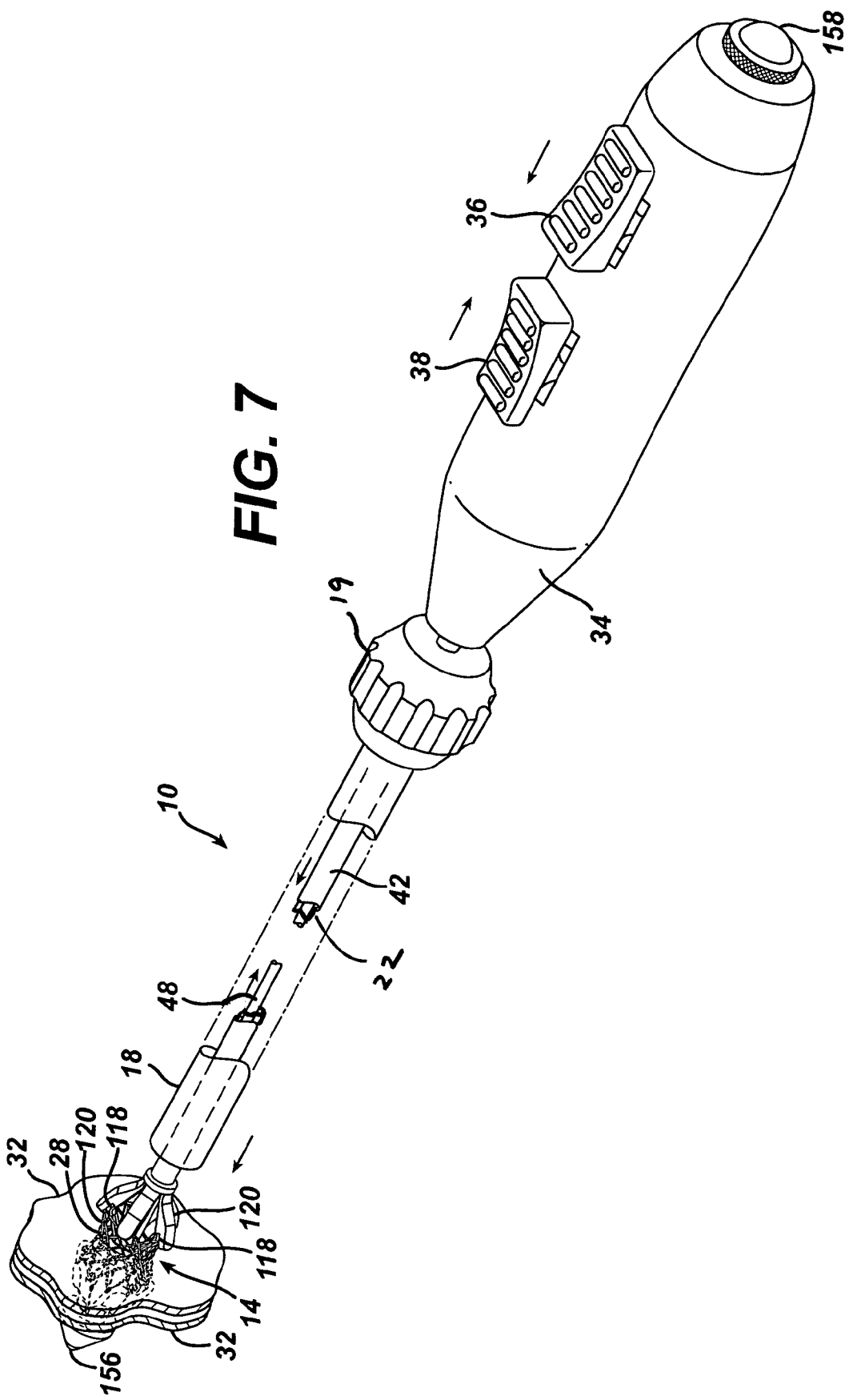
FIG. 7 is a perspective view of the applier of FIG. 1 in a partially actuated state.

In FIGS. 7, 9, a distal portion of the anastomotic ring device 12 are depicted in phantom to illustrate their actuated position. This phantom depiction is also suggestive of a clinical advantage of being able to view the deployment condition from a proximal point of view. Typically, an endoscope will view the anastomotic opening 28 from a proximal position. Returning to FIGS, 2-7, adding a deployment illumination feature to the applier 10 provides this ability to view deployment through translucent tissue walls. Specifically, an illumination power source (e.g., battery) 150 and control (e.g., switch) 152 are incorporated into the handle 34 with a conductor, depicted as a twisted wire pair 154 passing through the internal tube 48 to the tapered tip 24, which includes a proximally directed electroluminescence device 156. Alternatively conductive ink traces may be applied longitudinally down portions of the applier 10 to provide an electrical circuit to the tapered tip 24. An externally accessible push button 158 drives the power source 150 against the control 152, creating an illumination circuit with the electroluminescence device 156.

Alternatively or in addition, the molded actuating member 20 may be formed of a fluorescent or electroluminescent material that is either stimulated prior to insertion or receives light from a light source of the applier 10.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

As one example of an equivalent structure that may be used to implement the present invention, hydraulics, electronics, or pneumatics may be used to move cannula 13 relative to handle 34. Computer control could be used with electronics and a feedback loop to move tube 14 and to selectively tension a force element based on the amount of tissue force applied. As a further example of an equivalent structure that may be used to implement the present invention, robotics could be used with anastomosis device 10 attached to a controlled robotic arm that moves the mechanism of anastomosis device 10 to effect an anastomosis.

As a further example of an equivalent structure, cannula 13 could become a flexible tube, and the mechanisms within cannula 13 may become flexible to maneuver through a long lumen, such as a section of small bowel, to effect an anastomosis through a long, flexible lumen. Such a long, flexible tube may be used laparoscopically or endoscopically.

As a further example of an equivalent structure, applier 10 could have a long, rigid, curved tube, or a long, rigid, straight tube, and applier 10 could be placed through an obturator port and used laparoscopically or endoscopically. Length and curvature becomes advantageous in endoscopic or laproscopic surgery, especially when performing a surgical procedure on a bariatric patient. In either a rigid or a flexible form of an applier 10, restriction of gas flow through the instrument becomes advantageous when maintenance of a pneumoperitoneum is desired as in, for example, endoscopic surgery.

As a further example of an equivalent structure and method that may be used to implement the present invention, applier 10 may have a geometry small enough to be conveniently placed through the opening of a hand port used for hand-assisted laproscopic surgery, such as, for example, the Lap-Disk® hand port sold by Ethicon Endo-Surgery in Cincinnati, Ohio. A surgeon using applier 10 through a hand port may use an endoscope through a secondary port for visualization, and may also maintain a pneumoperitoneum. The surgeon may also make use of trocars, graspers, cutters, and other endoscopic instruments inserted through auxiliary ports to assist in grasping lumens or creating otomies in lumens to perform surgical procedures such as anastomoses.

As a further example of an equivalent structure and method that may be used to implement the present invention, a long, rigid version of applier 10, or a long, flexible embodiment of applier 10 may be used through an auxiliary port while tissue is manipulated by the surgeon using a hand placed through a hand port.

As other examples of equivalent structures, the surface of tapered tip 24 may take many forms advantageous for various types of tissue manipulation, such as a conical tipped nose that is blunted for low tissue trauma and for good visibility past the distal end. As another example, a nose that is fluted to allow torque to be applied to tissue. As yet a further example, a nose may have a convex curve for rapid dilation of an otomy in a short space or a nose having a concave surface for gentle dilation of friable tissue. An offset swept nose may be used because of its asymmetry for better visibility to one side and may be used to assist in manipulation by using its asymmetry to minimally grasp tissue. A spherical nose may be used to produce a short length for operation in limited space and to reduce the chance of tissue trauma. Combinations of these surfaces may also be advantageous, for example, a nose having a concave surface may also possess flutes. Other combinations may occur to one skilled in the art.

What is claimed is:

1. A surgical instrument comprising:
    a surgical instrument for implanting an anastomotic ring device comprising a woven tube of wire having outer loops or ends which thermally deform and evert when inserted into walls of two adjacent lumens at a luminal interface of an anastomotic site, the ends of the tube everting to form petals in a manner which holds the luminal interface of the anastomotic site into apposition, comprising:
        an actuating member formed of a plurality of proximal leaves and a plurality of distal leaves which each leaf outwardly actuates by a cantilevered, hinged relationship to a central portion of the actuating member, configured to receive an anastomotic ring and moveable between a cylindrical, unactuated position and a hollow rivet forming shape in response to a compressive actuating force;
        a plurality of distal engaging surfaces, each formed on a respective distal leaf spaced away from the central portion and positioned to engage a selected outer loop of a distal portion of the unactuated, cylindrical anastomotic ring for pulling the engaged outer loop proximally and outwardly during actuation;
        a plurality of proximal engaging surfaces, each formed on a respective proximal leaf spaced away from the central portion and positioned to engage a selected outer loop a proximal portion of the unactuated, cylindrical anastomotic ring for pulling the engaged outer loop distally and outwardly during actuation;
        a handle including an actuation mechanism for producing the compressive actuating force; and
        an elongate cannula connecting the handle to the actuating member and operably configured to position the distal leaves on a distal side of an anastomotic opening and to position the proximal leaves on a proximal side of the anastomotic opening, and configured to transfer the compressive actuating force from the handle to the actuating member wherein the handle is further operably configured to produce the compressive actuating force by producing a proximally directed longitudinal motion and a distally directed longitudinal motion, the elongate cannula operably configured to separately transfer the proximally and distally directed longitudinal motions respectively to distal and proximal portions of the actuating member to pivot corresponding distal and proximal leaves toward each other to actuate the anastomotic ring device from a cylinder shape to a hollow rivet shape, wherein the elongate cannula comprises a first tube connected to the proximal portion of the actuating member and a second tube slidingly received in the tube and connected to the distal portion of the actuating members and a third tube interposed between the first and second tubes and distally engaged to a central portion of the actuating member.

2. A surgical instrument, comprising:
    a cannula;
    an actuating member distally and laterally presented on the cannula for receiving a generally cylindrical anastomosis ring and formed of radially spaced proximal leaves and a plurality of distal leaves which each distal leaf outwardly actuates by a cantilevered, hinged relationship to a central portion of the actuating member;
    a first control operative to compress a longitudinal end of the actuating member toward a center of the actuating member to actuate a respective portion of the received anastomosis ring;
    a second control operative to compress another longitudinal end of the actuating member toward the center of the actuating member to actuate the other respective portion of the received anastomosis ring forming a hollow rivet shape;
    wherein the first and second controls are independently actuable to allow independent actuation of either longitudinal end of the actuating member; and
    wherein the longitudinal end of the actuating member controlled by the first control comprises a distal end positioned with a distal tissue lumen and wherein the longitudinal end of the actuating member controlled by the second control comprises a proximal end positioned within a proximal tissue lumen, the surgical instrument further comprising an illuminator connected to the cannula positioned to illuminate the distal longitudinal end of the actuating member to illuminate an apposition of the two tissue lumens.

3. A surgical instrument comprising:
    a surgical instrument for implanting an anastomotic ring device comprising a woven tube of wire having outer loops or ends which thermally deform and evert when inserted into walls of two adjacent lumens at a luminal interface of an anastomotic site, the ends of the tube everting to form petals in a manner which holds the luminal interface of the anastomotic site into apposition, comprising:

an actuating member formed of a plurality of proximal leaves and a plurality of distal leaves which each leaf outwardly actuate by a cantilevered, hinged relationship to a central portion of the actuating member, configured to receive an anastomotic ring and moveable between a cylindrical, unactuated position and a hollow rivet forming shape in response to a compressive actuating force;

a plurality of distal engaging surfaces, each formed on a respective distal leaf spaced away from the central portion and positioned to engage a selected outer loop of a distal portion of the unactuated, cylindrical anastomotic ring for pulling the engaged outer loop proximally and outwardly during actuation;

a plurality of proximal engaging surfaces, each formed on a respective proximal leaf spaced away from the central portion and positioned to engage a selected outer loop a proximal portion of the unactuated, cylindrical anastomotic ring for pulling the engaged outer loop distally and outwardly during actuation;

a handle including an actuation mechanism for producing the compressive actuating force;

an elongate cannula connecting the handle to the actuating member and operably configured to position the distal leaves on a distal side of an anastomotic opening and to position the proximal leaves on a proximal side of the anastomotic opening, and configured to transfer the compressive actuating force from the handle to the actuating member wherein the handle is further operably configured to produce the compressive actuating force by producing a proximally directed longitudinal motion and a distally directed longitudinal motion, the elongate cannula operably configured to separately transfer the proximally and distally directed longitudinal motions respectively to distal and proximal portions of the actuating member to pivot corresponding distal and proximal leaves toward each other to actuate the anastomotic ring device from a cylinder shape to a hollow rivet shape; and an electrical illumination source attached to a distal end of the cannula distal to the actuating member and directing illumination proximally toward the actuating member and comprising a control operably connected proximate to the distal portion of the actuating member.

4. The surgical instrument of claim 3, wherein the actuating member comprises a light transmissive material.

5. The surgical instrument of claim 3, wherein the actuating member comprises an electroluminescent material.

* * * * *